United States Patent [19]

Skotnicki

[11] Patent Number: 4,902,685
[45] Date of Patent: Feb. 20, 1990

[54] 2-AMINO-3-CYANO-BICYCLIC PYRIDINES/PYRAZINES AS INHIBITORS OF INTERLEUKIN 1

[75] Inventor: Jerauld S. Skotnicki, Chadds Ford, Pa.

[73] Assignee: American Home Products Corporation, New York, N.Y.

[21] Appl. No.: 233,182

[22] Filed: Aug. 17, 1988

[51] Int. Cl.[4] .................. A61K 31/495; A61K 31/44; C07D 471/04
[52] U.S. Cl. .................................... 514/249; 514/254; 514/256; 514/259; 514/300; 544/284; 544/295; 544/298; 544/333; 544/353; 544/354; 544/355; 544/405; 544/350; 546/122
[58] Field of Search ............... 544/350, 284, 295, 298, 544/333, 353, 354, 355, 405; 546/122; 514/249, 254, 256, 259, 300

[56] References Cited

PUBLICATIONS

Kurihara et al., *J. Heterocycl. Chem.*, 14, 1077 (1977).
Taylor et al., *J. Med. Chem.*, 20, 1215 (1977).
Taylor et al., *J. Org. Chem.*, 50, 1005 (1985).
Taylor et al., *Heterocycles*, 23, 1703 (1985).

Primary Examiner—Mary C. Lee
Assistant Examiner—Bernard I. Dentz
Attorney, Agent, or Firm—George Tarnowski

[57] ABSTRACT

There are disclosed compounds of the formula

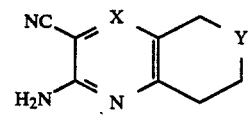

wherein
X is CH or N
Y is $CHR^1$, $NR^2$, O or S;
$R^1$ is lower alkenyl, lower alkynyl, or unsubstituted or substituted phenyl, naphthyl, pyridyl, pyrazinyl, pyrimidinyl, quinolyl, quinazolinyl or quinoxalinyl, wherein the substituents are selected from halo, lower alkyl, lower alkoxy, carboxy, lower alkoxycarbonyl, lower alkyl sulfonyl, nitro, cyano, trifluoromethyl, hydroxy, mercapto and lower alkylthio; and
$R^2$ is hydrogen, lower alkyl, lower alkenyl, lower alkynyl, or unsubstituted or substituted phenyl, naphthyl, pyridyl, pyrazinyl, pyrimidinyl, quinolyl, quinazolinyl or quinoxalinyl, wherein the substituents are selected from halo, lower alkyl, lower alkoxy, carboxy, lower alkoxycarbonyl, lower alkylsulfonyl, nitro, cyano, trifluoromethyl, hydroxy, mercapto and lower alkylthio, with the proviso that when $R^2$ is substituted phenyl, the substituent is other than carboxy or lower alkoxycarbonyl, which, by virtue of their ability to inhibit interleukin 1, are of use as antiinflammatory agents and in treatment of disease states involving enzymatic tissue destruction, and there is also disclosed a method of using such compounds in the treatment of immunoinflammatory, inflammatory/proliferative and enzymatic tissue destruction conditions.

8 Claims, No Drawings

2-AMINO-3-CYANO-BICYCLIC PYRIDINES/PYRAZINES AS INHIBITORS OF INTERLEUKIN 1

This invention relates to novel compounds possessing interlukin 1 (IL 1) antagonist activity and having antiinflammatory activity.

Interleukin 1 (IL 1) is a peptide hormone exhibiting a number of immune and inflammatory actions [Dinarello, *Rev. Inf. Dis.* 6, 51 (1984)]. IL 1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL 1 was originally shown to augment the proliferation of T lymphocytes for which it was named lymphocyte activating factor (LAF), and is believed to be important for the generation of T cell-dependent immune responses.

There is evidence to suggest a relationship between IL 1 and pathology in various diseases, particularly immunoinflammatory disorders such as rheumatoid arthritis [Dinarello et al., *Ann. Rev. Med.*, 37, 173 (1986)]. IL 1 induces acute inflammatory responses producing soft tissue swelling (edema and erythema) [Granstein et al., *J. Clin. Invest.*, 77, 1010 (1986)]. It is a chemoattractant for polymorphonuclear leukocytes (PMN) and induces the activation and migration of these cells into tissues. IL 1 also stimulates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986] and hypothalamic tissue. This effect on the hypothalamus is thought to be responsible for fever production. IL 1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 181 (1977) and Postlethwaite et al., *J. Exp. Med.*, 157, 801 (1983)]. Furthermore, IL 1 induces hyperproliferation of dermal and synovial fibroblasts and is a potent inducer of bone resorption (Wood et al., *J. Immunol.*, 134, 895 (1985) and Gilman and Kimball, *Agents and Actions*, 16, 468 (1985)].

Finally, IL 1 mediates acute phase reactions including alterations in plasma divalent cations, increased synthesis by liver cells of acute phase proteins (C-reactive protein, serum amyloid A, etc.) and fever. Accordingly, compounds which have IL 1 antagonist activity and thereby inhibit the biological effects of IL 1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlanta, 1983], psoriasis and other inflammatory/proliferative skin disorders as well as diseases in which the secretion of collagenase (and other tissue hydrolysing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It is now been found that certain novel 2-amino-3-cyanopyridines/-pyrazines antagonize the activity of IL 1, and so are useful as antiinflammatory agents and in the treatment of pathologies whose etiology is collagenase-based tissue destruction. The present invention provides novel compounds having the formula:

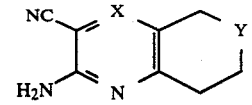

wherein
X is CH or N;
Y is $CHR^1$, $NR^2$, O or S; and
$R^1$ is lower alkenyl, lower alkynyl, or unsubstituted or substituted phenyl, naphthyl, pyridyl, pyrazinyl, pyrimidinyl, quinolyl, quinazolinyl or quinoxalinyl, wherein the substituents are selected from halo, lower alkyl, lower alkoxy, carboxy, lower alkoxycarbonyl, lower alkylsulfonyl, nitro, cyano, trifluoromethyl, hydroxy, mercapto and lower alkylthio; and
$R^2$ is hydrogen, lower alkyl, lower alkenyl, lower alkynyl, or unsubstituted or substituted phenyl, naphthyl, pyridyl, pyrazinyl, pyrimidinyl, quinolyl, quinazolinyl or quinoxalinyl, wherein the substituents are selected from halo, lower alkyl, lower alkoxy carboxy, lower alkoxycarbonyl, lower alkylsulfonyl, nitro, cyano, trifluoromethyl, hydroxy, mercapto and lower alkylthio, with the proviso that when $R^2$ is substituted phenyl, the substituent is other than carboxy or lower alkoxycarbonyl.

The invention further provides a method for treating immunoinflammatory conditions such as rheumatoid arthritis, osteoarthritis, tendinitis, bursitis, inflammatory/proliferative skin disorders such as psoriasis, as well as disease states involving enzymatic tissue destruction, such as rheumatoid arthritis joint destruction, periodontal disease, tumor invasiveness, corneal ulcerations and the like. The method of treating immunoinflammatory, inflammatory/proliferative and enzymatic tissue destruction conditions comprises administering to a mammal so afflicted an effective amount of a compound having the formula:

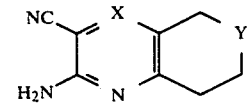

wherein
X is CH or N.
Y is $CHR^1$, $NR^1$, O or S; and
$R^1$ is hydrogen, lower alkyl, lower alkenyl, lower alkynyl, or unsubstituted or substituted phenyl, naphthyl, pyridyl, pyrazinyl, pyrimidinyl, quinolyl, quinazolyl or quinoxalinyl, wherein the substituents are selected from halo, lower alkyl, lower alkoxy, carboxy, lower alkoxycarbonyl, lower alkylsulfonyl, nitro, cyano, trifluoromethyl, hydroxy, mercapto and lower alkylthio.

The terms "lower alkyl", "lower alkenyl", "lower alkynyl" and "lower alkoxy" refer to moieties having 1 to 6 carbon atoms in the carbon chain. The term "halo" refers to fluoro, chloro and bromo.

The especially preferred compounds are those having the formula

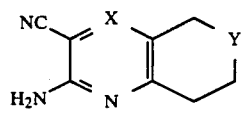

X is CH or N;
Y is CH$_2$ or NR$^1$, and
R$^1$ is 4-cyanophenyl or 4-methylsulfonylphenyl.

The compounds of the invention can be prepared by several routes. According to one route, 1,4-dioxa-8-azaspiro[4.5]decane is reacted with a suitable halo-R$^1$ reactant, and following ketal hydrolysis, the resultant intermediate is reacted with pyrrolidine in the presence of an acid such as toluenesulfonic acid to yield an intermediate N-substituted-(4-pyrrolidinyl)pyridine:

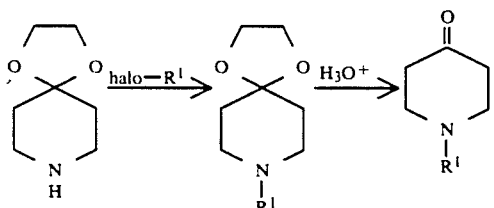

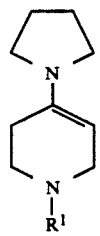

In the final step, the N-substituted-(4-pyrrolidinyl)pyridine is reacted with either ethoxymethylenemalononitrile or (O-p-tosylisonitroso)malononitrile followed by reaction with ammonia to yield the desired final product:

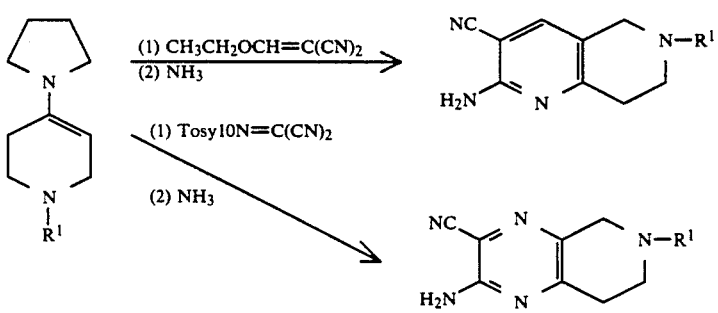

Compounds in which Y is CHR$^1$ can be prepared as outlined above, however, the starting material in this instance is 1-(pyrrolidino)-1-cyclohexene:

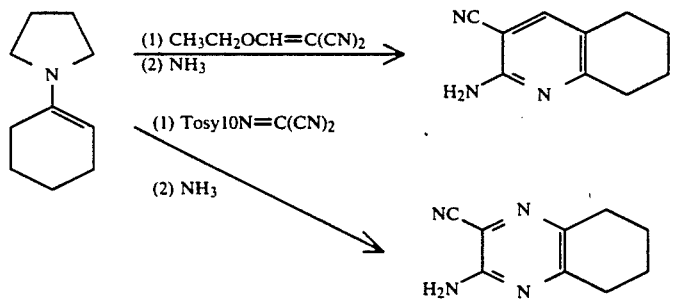

The starting materials used in the above outlined preparative sequences are all available commercially or can be prepared by conventional methods disclosed in the chemical literature.

The compounds of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like.

When the compounds of the invention are employed as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosage less than the optimum dose of the compound. Thereafter the dosage is increased until the optimum effect under the circumstances is reached. In general, the compounds of the invention are most desirably administered at a concentration that will generally afford effective results without causing any harmful or deleterious side effects and can be administered either as a single unit dose, or if desired, the dosage may be divided into convenient subunits administered at suitable times throughout the day.

The interleukin 1 antagonist activity, as well as the antiinflammatory effects of the compounds of the invention may be demonstrated by standard pharmacological procedures, which are described more fully in the examples given hereinafter.

These procedures illustrate the ability of the compounds of the invention to inhibit the IL 1-induced release of neutral protease from articular chondrocytes.

The following examples show the preparation and pharmacological testing of compounds within the invention.

EXAMPLE 1

2-Amino-6-(4-cyanophenyl)-5,6,7,8-tetrahydro-1,6-naphthyridine-3-carbonitrile (a) 4-(1,4-Dioxa-8-azaspiro[4.5]dec-8-yl)benzonitrile A mixture of 10 g (0.0825 mol) p-fluorobenzonitrile, 47 g (0.382 mol) of 1,4-dioxa-8-azaspiro[4.5]decane, 17 g (0.123 mol) of $K_2CO_3$, and 100 ml of acetonitrile is stirred at 90°–100° C. for three days. The reaction mixture is allowed to cool to ambient temperature, diluted with water and extracted with methylene chloride. The combined extracts are washed with brine, dried over $Na_2SO_4$, and concentrated in vacuo to give a pasty solid. Trituration with ethyl ether furnishes 13.4 g (67%) of title compound: m.p. 134°–135° C.; IR (KBr) 2210 and 1600 cm$^{-1}$; NMR (CDCl$_3$) δ 7.48 (d, 2H), 6.88 (d, 2H), 4.0 (s, 4H), 3.58–3.40 (m, 4H), and 1.90–1.70 (m, 4H).

(b) 4-(4-Oxo-1-piperidinyl)benzonitrile

A mixture of 12 g (0.049 mol) of the ketal of (a), 120 ml of 10% $H_2SO_4$ solution, and 60 ml of tetrahydrofuran is stirred at ambient temperature for 4 days. The reaction mixture is diluted with water and extracted with methylene chloride. The combined organic extracts are dried over $Na_2SO_4$ and concentrated in vacuo to give a pasty solid. Trituration with ethyl ether provides 4.6 g (46%) of title compound: m.p. 100°–101° C.; IR (KBr) 2220 and 1700 cm$^{-1}$; NMR (CDCl$_3$)δ 7.54 (d, 2H), 6.90 (d, 2H), 3.88–3.66 (m, 4H), and 2.70–2.52 (m, 4H).

(c) 4-[3,6-Dihydro-4-(1-pyrrolidinyl)-1(2H)-pyridinyl]benzonitrile

A solution of 24 g (0.1199 mol) of the compound of (b), 15 ml (12.78 g/0.1796 mol) of pyrrolidone, 240 mg of p-toluenesulfonic acid, and 100 ml of benzene is stirred at reflux with the azeotropic removal of water for 6 hours. After cooling, the resulting precipitate is collected and triturated with ethyl ether to afford 20 g (66%) of title compound: m.p. 126°–129° C.; IR (KBr) 2200, 1635, and 1600 cm$^{-1}$; $^1$H NMR (CDCl$_3$) δ 7.48 (d, 2H), 6.7 (d, 2H), 4.3–4.1 (m, 1H), 3.95–3.45 (m, 4H), 3.2–2.85 (m, 4H), 2.65–2.25 (m, 2H), and 1.95–1.75 (m, 4H).

Analysis for: $C_{16}H_{19}N_3$: Calculated: C, 75.85; H, 7.56; N, 16.59. Found: C, 75.42; H, 7.51; N, 16.57.

(d) 2-Amino-6-(4-cyanophenyl)-5,6,7,8-tetrahydro-1,6-naphthyridine-3-carbonitrile To a mixture of 4.34 g (0.0355 mol) of ethoxymethylenemalononitrile and 300 ml of tetrahydrofuran at −40° C. is added portionwise 9.0 g (0.0355 mol) of the compound of c). After 30 min, the mixture is allowed to warm to 0° C. for 3 hrs. The solvent is removed in vacuo. The residue is treated with 300 ml of saturated ammonia in methanol at 0° C. The reaction mixture is stirred overnight at ambient temperature, then diluted with water and the resulting precipitate is collected to give 2 g (20%) of title compound. The analytical sample is prepared by recrystallization from ethanol: m.p. 233°–237° C. (dec); IR (KBr) 3400, 3300, 3200, 2220, 1650, and 1610 cm$^{-1}$; NMR (DMSO-d$_6$)δ 8.75 (s, 1H), 8.62 (d, 2H), 7.02 (d, 2H), 6.75 (br-s, 2H, exchangeable), 4.40 (s, 2H), 3.70 (t, 2H), and 2.82 (t, 2H).

Analysis for: $C_{16}H_{13}N_5$: Calculated: C, 69.80; H, 4.76; N, 25.46. Found: C, 65.56; H, 4.97; N, 23.72.

EXAMPLE 2

2-Amino-6-(4-cyanophenyl)-5,6,7,8-tetrahydropyrido[3,4-b]pyrazine-3-carbonitrile To a mixture of 600 mg (0.0024 mol) of (O-p-tosylisonitroso)malononitrile, 25 ml of tetrahydrofuran, and 0.2 ml (0.0025 mol) of pyridine, at −35° C., is added portionwise a mixture of 600 mg (0.0024 mol) of the compound of (1c) above and 25 ml of tetrahydrofuran. After 2 hrs., the reaction mixture is allowed to warm to 0° C. for 30 min. To the reaction mixture at 0° C. is added 30 ml of saturated ammonia in methanol. The reaction mixture is stirred overnight at ambient temperature, diluted with water, and extracted with methylene ether. The combined extracts are dried (Na$_2$SO$_4$), and concentrated in vacuo to give an oily solid. Trituration with ethanol affords 400 mg (60%) of title compound, recrystallization from ethanol/water furnishes an analytical sample: IR (KBr) 3400, 3330, 3200, 2220, 1640, and 1610 cm$^{-1}$; NMR (CDCl$_3$) δ 7.60 (d, 2H), 6.98 (d, 2H), 5.20 (br-s, 2H-exchangeable), 4.52 (s, 2H), 3.81 (t, 2H), and 3.08 (t, 2H).

Analysis for: C$_{15}$H$_{12}$N$_6$: Calculated: C, 65.20; H, 4.38; N, 30.42. Found: C, 64.61; H, 4.76; N, 27.39.

EXAMPLE 3

2-Amino-5,6,7,8-tetrahydro-6-[4-(methylsulfonyl)-phenyl]-1,6-naphthyridine-3-carbonitrile (a)

8-[4-Methylsulfonyl)phenyl]-1,4-dioxa-8-azaspiro[4.5]-decane

A mixture of 10 g (0.057 mol) of p-fluorophenyl methyl sulfone, 8.72 g (0.063 mol) of K$_2$CO$_3$, 24.66 g (0.172 mol) of 1,4-dioxa-8-azaspiro[4.5]decane, and 50 ml of acetonitrile is stirred overnight at 90°–100° C. After cooling, the mixture is diluted with water and extracted with methylene chloride. The combined extracts are washed with brine, dried over Na$_2$SO$_4$, and concentrated in vacuo. Trituration with ethyl ether affords 13.11 g (77%) of the title compound as a white solid: m.p. 192°–194° C.; IR (KBr) 1588, 1369, and 1290 cm$^{-1}$; NMR (CDCl$_3$)δ 7.74 (m, 2H), 6.96 (m, 2H), 4.02 (s, 4H), 3.54 (m, 4H), 3.03 (s, 3H), and 1.81 (m, 4H).

Analysis for: C$_{14}$H$_{19}$NO$_4$S: Calculated: C, 56.54; H, 6.44; N, 4.71. Found: C, 56.37; H, 6.55; N, 4.97.

(b) 1-[4-(Methylsulfonyl)phenyl]-4-piperidinone

A mixture of 12.97 g (0.0436 mol) of the ketal of b) and 200 ml of 10% H$_2$SO$_4$/tetrahydrofuran (2:1) solution is stirred at 60°–70° C. for 4 hrs. and is then allowed to stand at room temperature for 3 days. The mixture is diluted with water and extracted with methylene chloride. The combined extracts are washed with brine, dried over Na$_2$SO$_4$, and concentrated in vacuo. Trituration with ethyl ether gives 10.07 g (91%) of title compound as a white solid: m.p. 183°–185° C.; IR (KBr) 3410, 1710, 1585, and 1160 cm$^{-1}$; NMR (CDCl$_3$)δ 7.79 (d, 2H), 6.98 (d, 2H), 3.79 (t, 4H), 3.04 (s, 3H), and 2.61 (t, 4H).

Analysis for: C$_{12}$H$_{15}$NO$_3$S: Calculated: C, 56.89; H, 5.97; N, 5.53. Found: C, 57.36; H, 6.23; N, 5.88.

(c)

1,2,3,6-Tetrahydro-1-[4-(methylsulfonyl)phenyl]-4-(1-pyrrolidinyl)pyridine

A solution of 24 g (0.0947 mol) of the compound of (b), 12 ml (10.2 g/0.143 mol) of pyrrolidine, 240 mg of p-toluenesulfonic acid and 150 ml of benzene is heated at reflux with the azeotropic removal of water for 6 hours. After cooling the resulting precipitate is collected and triturated with ethyl ether to afford 22.5 g (78%) of title compound: m.p. 141°–143° C.; IR (KBr) 1650, 1580, 1300, and 1130 cm$^{-1}$; NMR (CDCl$_3$)δ 7.75 (d, 2H), 6.85 (d, 2H), 4.30–4.10 (m, 1H), 3.95–3.45 (m, 4H), 3.25–2.85 (m, 4H) 3.05 (s, 3H), 2.65–2.30 (m, 2H), and 1.95–1.70 (m, 4H).

Analysis for: C$_{16}$H$_{22}$N$_2$O$_2$S: Calculated: C, 62.71; H, 7.24; N, 9.14. Found: C, 62.46; H, 7.04; N, 9.01.

(d)

2-Amino-5,6,7,8-tetrahydro-6-[4-(methylsulfonyl)-phenyl]-1,6-naphthyridine-3-carbonitrile To a mixture of 4.38 g (0.0359 mol) of ethoxymethylenemalononitrile and 300 ml of tetrahydrofuran at −40° C. is added portionwise 11 g (0.0359 mol) of the compound of c). After 30 min, the mixture is allowed to warm to 0° C. for 3 hrs. The solvent is removed in vacuo and the residue is treated with 300 ml of a saturated solution of ammonia in methanol at 0° C. The reaction mixture is stirred overnight at ambient temperature, then diluted with water. The resulting precipitate is collected to give 1.2 g (12%) of title compound. An analytical sample is prepared by recrystallization from ethanol: m.p. 204°–208° C. (dec); IR (KBr) 3400, 3340, 3180, 2210, 1650, and 1600 cm$^{-1}$; NMR (DMSO-d$_6$)δ 7.75 (s, 1H), 7.70 (d, 2H), 7.08 (d, 2H), 6.72 (br-s, 2H, exchangeable), 4.40 (s, 2H), 3.72 (t, 2H), 3.08 (s, 3H), and 2.82 (t, 2H).

Analysis for: C$_{16}$H$_{16}$N$_4$SO$_2$: Calculated: C, 58.52; H, 4.97; N, 17.06. Found: C, 58.10; H, 5.03; N, 14.52

EXAMPLE 4

2-Amino-5,6,7,8-tetrahydro-3-quinoxalinecarbonitrile

To a mixture of 33 g (0.1324 mol) of (O-p-tosylisonitroso)-malononitrile, 300 ml of tetrahydrofuran, and 11 ml (0.136 mol) of pyridine at −35° C. is added portionwise a mixture of 20 g (0.1322 mol) of 1-(pyrrolidino)-1-cyclohexene and 300 ml of tetrahydrofuran. After 2 hrs., the reaction mixture is allowed to warm to 0° C. for 30 min. To the reaction mixture at 0° C. is added 300 ml of a saturated solution of ammonia in methanol. The reaction mixture is stirred at ambient temperature overnight, then diluted with water, and extracted with methylene chloride. The combined extracts are dried (Na$_2$SO$_4$), and concentrated in vacuo to give an oily solid. Trituration with ethanol furnishes 4.7 g (20%) of title compound. Recrystallization from ethanol provides an analytical sample: m.p. 200°–202° C.; IR (KBr) 3400, 3340, 3200, 2240, 1665, and 1580 cm$^{-1}$; NMR (DMSO-d$_6$) δ 6.90 (br-s, 2H), exchangeable), 2.85–2.55 (m, 4H), and 1.90–1.55 (m, 4H).

Analysis for: C$_9$H$_{10}$N$_4$: Calculated: C, 62.05; H, 5.79; N, 32.16. Found: C, 62.00; H, 5.74; N, 31.59.

EXAMPLE 5

2-Amino-5,6,7,8-tetrahydro-3-quinolinecarbonitrile

To a mixture of 16 g (0.131 mol) of ethoxymethylenemalononitrile and 450 ml of tetrahydrofuran at −35° C. is added portionwise a mixture of 20 g (0.1322 mol) of 1-(pyrrolidino)-1-cyclohexene and 300 ml of tetrahydrofuran. After 2 hrs., the reaction mixture is allowed to warm to 0° C. for 30 min. To the reaction mixture at 0° C. is added 300 ml of a saturated solution of ammonia in methanol. The reaction mixture is stirred overnight at ambient temperature, diluted with water, and extracted with methylene chloride. The combined extracts are dried (Na$_2$SO$_4$) and concentrated in vacuo to give an oily solid. Trituration with ethanol affords 4.3 g (19%) of title compound. Recrystallization from ethanol provides an analytical sample: m.p. 192°–193° C.; IR (KBr) 3430, 3320, 3170, 2220, 1645, and 1600 cm$^{-1}$; NMR (DMSO-d$_6$)δ 7.55 (s, 1H), 6.45 (br-s, 2H, exchangeable), 2.7–2.35 (m, 4H, partially obscured by DMSO), and 1.85–1.55 (m, 4H).

Analysis for: C$_{10}$H$_{11}$N$_3$: Calculated: C, 69.34; H, 6.40; N, 24.26. Found: C, 69.23; H, 6.33; N, 24.11.

EXAMPLE 6

The ability of the compounds of the inventions to inhibit interleukin 1 is measured by the ability of the test compounds to inhibit the IL 1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls. of Nembutal. The knee joints of both legs are resected and the articular surfaces are exposed. Cartilate slices are obtained using a scalpel and are placed in a tissue culture dish (100 mm diameter) containing 10 mls of Hank's balanced salt solution (HBSS). The chrondrocytes within the cartilage slices are then liberated by a series of enzyme digestions. The slices are incubated for 10 min. at 37° C. in 0.05% hyaluronidase (Sigma H-3884), rinsed with HBSS and incubated with 0.2% trypsin (Sigma T-2395)for 10 min. at 37° C. The slices are rinsed again and incubated for 10 mins. at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% $CO_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then placed into 24-well tissue culture plates ($2 \times 10^5$ cells/well) and incubated at 37° C. until confluent (usually 4-6 days).

Stimulation of chondrocytes and drug treatment:

The confluent chondrocytes are rinsed twice with serum-free Ham's F-12 medium and 1 ml is added to each well. Fifty µl of purified human IL 1 (100 Units/ml; Genzyme Corporation, Boston, MA) is then added to stimulate these cells to secrete neutral protease. To measure drug effects, the cells are treated with test compound 10 min. prior to addition of IL 1. The standard screening dose is 10 µM. Twenty-four hours after IL 1 stimulation, supernatant fluids are collected and assayed for neutral protease activity.

Neutral protease assay:

The neutral protease activity of chrondrocyte supernatant fluids is determined by their ability to degrade an insoluble protease substrate, azocoll (Sigma). Supernatants are treated for 10 min. at room temperature with 350 µM p-aminophenylmercuric acetate to activate the latent enzyme. Three hundred µl of supernatant is then mixed with 500 µl of a 20 mg/ml suspension of azocoll and incubated at 37° C. for 18-24 hrs. with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chrondrocytes relative to enzyme activity of supernatants from vehicle-treated chondrocytes as follows:

% Inhibition of protease Secretion =

$$\frac{(A_{520}) \text{ Untreated Supernatant} - A_{520} \text{ Drug Treated Supernatant}}{A_{520} \text{ Untreated Supernatant}} (\times 100)$$

Where tested in this assay, the compounds of the invention gave the following results:

| Compound of Example No. | Dose (µM) | % Inhibition (I.S.D.) |
|---|---|---|
| 1 | 10 | 18 |
| 2 | 10 | 37 |
| 3 | 10 | 59 |
| 4 | 10 | 41 |
| 5 | 10 | 59 |
|   | 1  | 60 |

The results show that the compounds tested exhibit a moderate to quite significant inhibition of IL 1-induced protease secretion.

What is claimed is:

1. A compound having the formula

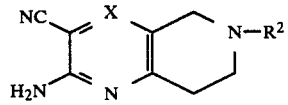

wherein
X is CH or N; and
$R^2$ is hydrogen, lower alkyl, lower akenyl, lower alkynyl, or unsubstituted or substituted phenyl, naphthyl, pyridyl, pyrazinyl, primidinyl, quinolyl, quinazolinyl or quinoxalinyl, wherein the substituents are selected from halo, lower alkyl, lower alkoxy, carboxy, lower alkoxycarbonyl, lower alkylsulfonyl, cyano, nitro, trifluoromethyl, hydroxy, mercapto and lower alkylthio, with the proviso that when $R^2$ is substituted phenyl, the substituted is other than carboxy or lower alkoxycarbonyl.

2. The compound of claim 1, having the name 2-amino-6-(4-cyanophenyl)-5,6,7,8-tetrahydro-1,6-naphthyridine-3-carbonitrile.

3. The compound of claim 1, having the name 2-amino-6-(4-cyanophenyl)-5,6,7,8-tetrahydropyrido[3,4-b]pyrazine-3-carbonitrile.

4. The compound of claim 1, having the name 2-amino-5,6,7,8-tetrahydro-6-[4-(methylsulfonyl)phenyl]-1,6-naphthyridine-3-carbonitrile.

5. A method for treating immunoinflammatory, inflammatory/proliferative and enzymatic tissue destruction conditions, comprising administering to a mammal so afflicted an effective amount of a compound having the formula

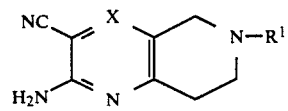

wherein
X is CH or N; and
$R^1$ is hydrogen, lower alkyl, lower alkenyl, lower alkynyl, or unsubstituted or substituted phenyl, naphthyl, pyridyl, pyrazinyl, pyrimidinyl, quinolyl, quinazolyl or quinoxalinyl, wherein the substituents are selected from halo, lower alkyl, lower alkoxy, carboxy, lower alkoxycarbonyl, lower alkylsulfonyl, cyano, nitro, trifluoromethyl, hydroxy, mercapto and lower alkylthio.

6. The method of claim 5, wherein the compound has the name 2-amino-6-(4-cyanophenyl)-5,6,7,8-tetrahydro-1,6-naphthyridine-3-carbonitrile.

7. The method of claim 5, wherein the compound has the name 2-amino-6-(4-cyanophenyl)-5,6,7,8-tetrahydropyrido[3,4-b]pyrazine-3-carbonitrile.

8. The method of claim 5, wherein the compound has the name 2-amino-5,6,7,8-tetrahydro-6-[4-(methylsulfonyl)phenyl]-1,6-naphthyridine-3-carbonitrile.

* * * * *